United States Patent [19]

Chao et al.

[11] 4,359,592

[45] Nov. 16, 1982

[54] MULTI-STAGE, ADSORPTION PROCESS FOR SEPARATING ORGANIC LIQUIDS FROM WATER

[75] Inventors: James C. Chao, West Nyack, N.Y.; Cheng-Yih Jenq, Princeton, N.J.

[73] Assignee: Hydrocarbon Research, Inc., Lawrenceville, N.J.

[21] Appl. No.: 246,534

[22] Filed: Mar. 23, 1981

[51] Int. Cl.³ .............................................. B01D 15/00
[52] U.S. Cl. ................................... 568/916; 210/694; 568/917
[58] Field of Search ............... 55/33, 35, 75; 210/670, 210/673, 677, 691, 694, 908; 568/840, 917, 916

[56] References Cited

U.S. PATENT DOCUMENTS 2,474,170  6/1949  Sulzbacher .......................... 568/411
4,130,484  12/1978  Marwil et al. ........................ 55/35

*Primary Examiner*—Ivars C. Cintins
*Attorney, Agent, or Firm*—Vincent A. Mallare; Fred A. Wilson

[57] ABSTRACT

Organic liquid-water solutions, such as 5–30 W % alcohol in water, are separated efficiently in a two-stage adsorption process using a bed of selected adsorbent material in each stage to produce a concentrated organic product. Each adsorbent is selected to effectively adsorb the minor component from the feed solution and thus provide a dehydrated alcohol product. In the first-stage adsorber bed, activated carbon is used to selectively adsorb the alcohol, after which the desorbed alcohol vapor is passed to a second-stage adsorber bed of molecular sieve adsorbent for virtually complete removal of the remaining water. The process provides a dehydrated alcohol liquid product preferably containing less than about 2 W % water, and requires low energy usage.

11 Claims, 2 Drawing Figures

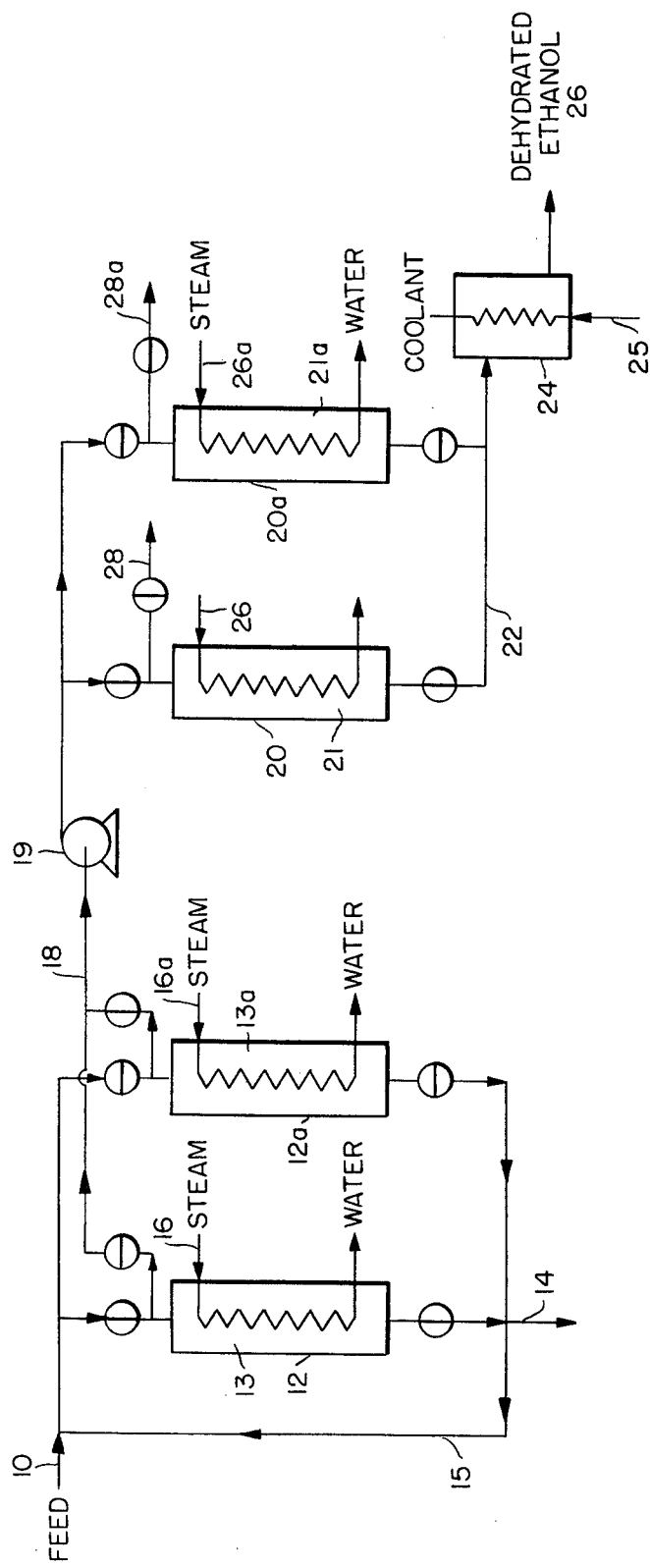

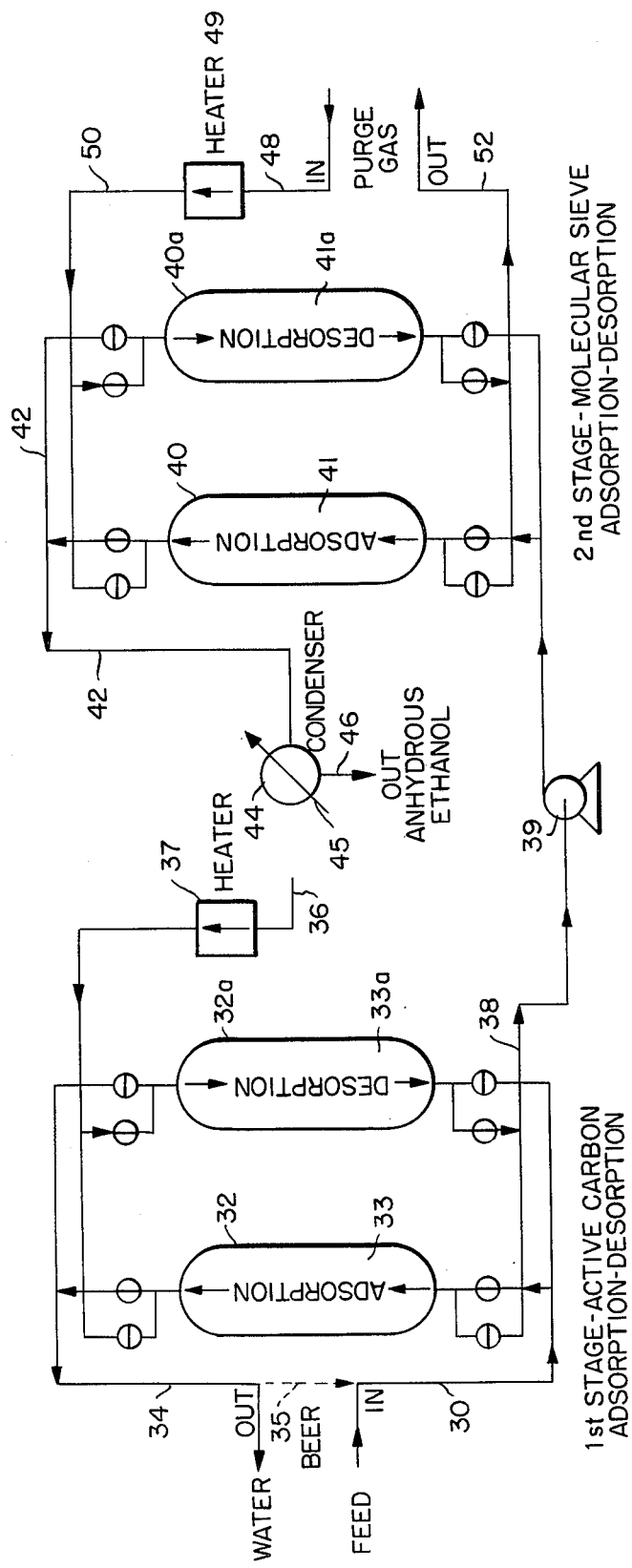

MULTI-STAGE, ADSORPTION PROCESS FOR SEPARATING ORGANIC LIQUIDS FROM WATER

BACKGROUND OF INVENTION

This invention pertains to the separation of organic liquids such as alcohols from water solutions containing same, using a multi-stage adsorption process.

Energy-efficient processes for separating alcohols, such as ethanol, from water solutions have been sought in recent years. The objective is to make fermentation ethanol an economic and attractive source of liquid fuels. Conventional distallation separation for ethanol-water solutions requires substantial energy, equivalent to 28–35% of the combustion energy of ethanol (84,800 Btu/gal). This undesirably high energy requirement is due to the multiple liquid-vapor phase changes inherent to fractionating distillation, which are energy intensive operations. Contrarily, adsorption processes for liquid-vapor separation are usually exothermic and require no energy input; only the desorption or releasing the adsorbed material requires some energy or heat input. Based on this concept, a multi-stage adsorption process for ethanol-water separation was conceived and developed which has low energy consumption and low investment costs, and thus is advantageous for the economic production of ethanol and other alcohols.

It is generally known that alcohol vapors can be dried by passing them over adsorbents that selectively adsorb water. Although drying of alcohols and various hydrocarbons by adsorption on molecular sieve is known, such processes are not attractive for removing major portions of water from solutions so as to provide dehydrated products. Thus, an energy-efficient adsorption process for removing major amounts of water from organic liquid solutions has been sought and would be very desirable and economically advantageous.

SUMMARY OF INVENTION

This invention discloses a multi-stage adsorption process for separating organic liquids such as alcohols from water solutions of such liquids, to produce a dehydrated organic liquid or liquid mixture product. The process uses an adsorbent material in each adsorption stage selected to provide effective adsorption characteristics for the minor component present in the feedstream to that stage. The organic liquid minor component of the feedstream solution, usually containing about 5 to 30 W % organic material, has a lower boiling point and is thus more volatile than water and, upon subsequent heating and desorption of the adsorbent beds, the organic vapor is preferentially removed and concentrated in the effluent vapor. The invention thus provides an energy-efficient process for dehydrating organic liquids such as alcohols and light hydrocarbons to less than about 10 W % and preferably to less than 2 W % water remaining therein.

In the first adsorption stage, the feedstream, such as an alcohol-water solution, is passed through a bed of adsorbent material having a preferential molecular attraction characteristic for the minor organic component. The adsorbent, such as activated carbon, preferentially adsorbs the organic minor component, such as ethanol, from a liquid solution such as filtered fermentation beer containing between about 5 to 20 W % ethanol. The carbon adsorbent in equilibrium with the ethanol-water solution conditions will gradually become substantially saturated with about 50 to 60 W % ethanol (carbon-free basis). The remaining water component which is not adsorbed passes on through the adsorbent bed, and can be recycled to the feedstream to minimize losses of the organic liquid product.

After the adsorbent becomes substantially saturated with the minor component; i.e. with the organic liquid or liquid mixture, the adsorption step is terminated and the feedstream switched to an alternate adsorption unit. Desorption of the saturated adsorbent is then carried out by heating it to a desorption temperature range of about 50°–100° C. A vapor stream is evolved containing the more volatile organic vapor, such as 70 to 80 W % ethanol, in equilibrium with the remainder or minor portion being water. Although dual adsorber units are preferably provided for the first-stage adsorption to complete the adsorption and desorption cycles for initial separation of ethanol from the ethanol-water mixture on a continuous basis, three or more adsorption vessels can be provided as needed and operated in timed sequence, depending on the relative time requirements for the adsorption and desorption steps for each adsorbent bed or vessel.

The ethanol-rich vapor desorbed from the first-stage adsorber is passed into a second-stage adsorption unit which contains an adsorbent material selected for effective adsorption of water vapor. This adsorbent is used to strip the remaining water from the alcohol-water vapor and provide a high-purity anhydrous alcohol product. Again, dual adsorber units are preferably provided for continuous operations, and the water-saturated adsorbent is regenerated by heating. However if desired, three or more adsorbent beds can be used in rotation, as required by the relative adsorption-desorption rates for the beds. Suitable adsorbent materials for the second-stage adsorption step have pore sizes selected to effectively adsorb water vapor, such as activated alumina, silica gel, and molecular sieves, with molecular sieves being preferred.

It is noted that, although two adsorption stages are usually adequate and are preferred for this process to dehydrate organic liquids such as alcohols, a third adsorption stage can be used for further removal of water vapor to obtain a higher purity organic product. The first stage provides for adsorption of up to about 60 W % ethanol on the first-stage adsorbent, which upon heating desorbs a vapor containing up to about 80 W % ethanol. This stage is followed by adsorption of up to the remaining 20 W % water in a second-stage adsorbent, or in both a second and third stage.

Because each adsorption stage in the process preferentially adsorbs the minor component from the feed solution, and because there are only two vaporization steps involved (for two-stage process), a minimum of energy is required and results in a highly efficient separation process. This process is much more efficient than the repeated evaporation-condensation steps usually required for an alcohol-water distillation separation process. As a result, for ethanol theoretically only about 7,200 Btu of energy are needed per gallon of ethanol produced, or only about 8.5% of the combustion energy of ethanol.

For desorption steps, heating each adsorbent bed to evolve the adsorbed fluid can be accomplished in any suitable way. The adsorbent bed can be heated either by using sensible heat, such as from embedded passageways carrying a hot fluid, or by electrical heating elements, or by passing a heated gas through the adsorbent bed to heat the bed and evolve the adsorbed fluid as a vapor stream. Desorption by the use of embedded fluid passageways carrying hot steam is usually preferred, because the desorbed organic vapor is not mixed with another contaminating gas.

DESCRIPTION OF DRAWING

FIG. 1 is a schematic sketch of a two-stage, two-adsorbent process for separation of alcohol-water solutions to provide dehydrated alcohol product, and using sensible heat for desorption.

FIG. 2 is a schematic diagram of an alternative two-stage adsorption process for alcohol-water separation, and utilizing heated gas for desorption.

DESCRIPTION OF PREFERRED EMBODIMENTS

As shown in FIG. 1, a liquid feedstream containing ethanol, such as from a beer fermentation process (not shown) containing 5-20 W % ethanol, is provided at 10 and introduced into adsorption vessel 12 containing a bed 13 of particulate activated carbon adsorbent. Usual operating conditions for the adsorption step are within the range of about 10°-60° C. temperature and 0-100 psig pressure. The ethanol in the feed solution is preferentially adsorbed on the carbon particles until they reach an equilibrium condition for the particular temperature and pressure conditions, and becomes substantially saturated with 50-60 W % ethanol. The remaining unadsorbed portion of the feed solution containing predominantly water and a small percentage of ethanol such as 1-4 W % is withdrawn from vessel 12 as stream 14. If desired, this stream 14 can be recycled at 15 to the feedstream 10 to minimize any losses of ethanol product from the process.

Adsorption of the ethanol minor portion from the feed is continued until the carbon particles are substantially saturated with ethanol at the existing conditions, such as usually after 1-8 hours depending on the size or length of the adsorber vessel 12 relative to the feed rate at 10, then the feedstream flow at 10 is switched to alternate adsorber 12a using a suitable valving arrangement. Such valving arrangements are well known and are not described in detail herein. The adsorbent bed 13 contained in adsorber 12, usually at reduced pressure, is then heated to the required desorption temperature by a suitable method, preferably indirectly by using internal passageway 16 carrying a hot fluid such as steam, and the adsorbent bed 13 is desorbed. Because of the lower boiling point of ethanol relative to water, an ethanol-enriched vapor is evolved from the bed 13 and withdrawn through conduit 18. Desorption of bed 13 is continued until the ethanol concentration in stream 18 declines to about 55 W % ethanol, with the remainder being water, after which heating and desorption is stopped. It is usually undesirable to continue the desorption to remove more than about 30 W % water from the activated carbon adsorbent bed 13 or 13a.

The ethanol-rich vapor at 18 containing 5-30 W % water is usually compressed at 19, and passed to second-stage adsorption unit 20, which contains a bed 21 of particulate adsorbent material such as molecular sieve selected to effectively strip the remaining water from the vapor stream. The adsorbent material used in adsorber 20 is selected to have average pore sizes which will admit and retain molecules of water but substantially exclude alcohols. Suitable adsorbents for use in adsorber 20 are zeolite molecular sieve, shaped activated carbon particles (glassy carbon), activated alumina, or silica gel, with molecular sieve Linde type 3A being preferred. Operating conditions for the second-stage adsorption are within the range of 20°-80° C. temperature and 10-100 psig pressure. A high-purity anhydrous ethanol vapor product stream is withdrawn at 22 usually containing less than about 2 W % water. Stream 22 is condensed at 24 using a suitable coolant at 25 to produce a dehydrated ethanol liquid stream at 26.

After the adsorbent bed 21 in adsorber 20 becomes substantially saturated with water, the vapor flow in conduit 18 is switched to alternate adsorber 20a. The adsorbent bed 21 in adsorber 20 is then heated to a desorption temperature range of 80°-100° C., either indirectly by means of embedded steam coils 26, or directly by passing a heated inert gas through the bed. The adsorbed water vapor is thus desorbed and removed from the bed through conduit 28. The regenerated adsorber 20 is then ready for reintroduction of vapor stream 18 from the first-stage, adsorption unit 12 or 12a.

Although use of dual-adsorber vessels have been described for both the first and second stages of adsorption for the continuous separation of alcohols from water solutions containing same, it is understood that three or more adsorbent beds could be used in timed sequence for each stage depending upon the required relative adsorption and desorption rates, with one bed usually always being desorbed.

Although FIG. 1 shows the ethanol-water feedstream preferably flowing downwardly through first-stage adsorber 12, with the desorbed ethanol vapor being preferably evolved from the top of adsorber 12a, the opposite flow direction could be used, as shown in the FIG. 2 embodiment. Similarly, ethanol-enriched vapor stream 18 is shown in FIG. 1 preferably flowing downwardly through second-stage adsorber 20, with water vapor stream 28 being evolved from the top of adsorber 20a; however, the opposite flow directions could be used, as shown in FIG. 2. It is also understood that other adsorption-desorption flow arrangements could be used, such as utilizing a continuous circulating flow of adsorbent material to provide continuous adsorption and desorption of the minor components from the feedstreams.

Although an indirect, steam-heated desorption arrangement is shown in FIG. 1 and such use of internal heating coils is usually preferred, alternatively, a direct gas-heated regeneration scheme can be employed as shown in the FIG. 2 embodiment. In FIG. 2, an ethanol-water feedstream 30 containing 5-15 W % ethanol is introduced into adsorption vessel 32 containing a bed 33 of particulate activated carbon adsorbent. Similarly as for FIG. 1, the ethanol in the feed solution is preferentially adsorbed on the carbon particles until they become substantially saturated at the particular operating conditions with about 50-60 W % ethanol. The remaining unadsorbed portion of the feed solution containing mainly water is withdrawn from vessel 32 as stream 34. Similarly as for FIG. 1, stream 34, which contains a small percentage of ethanol such as 1-4 W % ethanol, is recycled at 35 to feedstream 30 to minimize any losses of ethanol product from the process.

After the adsorption of ethanol from feedstream 30 has continued until the adsorbent 33 is substantially saturated with ethanol at the particular operating conditions, the feedstream is switched to alternate adsorber vessel 32a using a suitable valving arrangement. The adsorbent bed 33 is then heated at reduced pressure by an inert gas stream 36, which is heated at heater 37 and passed through adsorbent vessel 32a to heat the adsorbent bed 33a sufficient to desorb the alcohol vapor therefrom. Ethanol-enriched vapor is evolved from the bed and withdrawn through conduit 38. Desorption is continued until the ethanol concentration in 38 declines to about 55 W % ethanol with the remainder being water, after which the heating and desorption are terminated. It is usually desired to continue the desorption until at least about 30 W % water is removed from the activated carbon adsorbent bed 32a.

The resulting ethanol-rich vapor at 38 containing 5-30 W % water is usually compressed at 39 to 10-50 psig pressure and passed to second-stage adsorption unit 40, which contains a bed 41 of particulate adsorbent material, such as preferably molecular sieve, selected to effectively strip the vapor stream of its remaining water. A high-purity anhydrous ethanol vapor product usually containing less than about 1 W % water is withdrawn at 42, and passed to condenser 44, where the alcohol vapor is condensed by coolant 45 to produce dehydrated ethanol liquid product at 46.

After the adsorbent bed in 40 becomes substantially saturated with water, the flow in conduit 38 is switched to alternate adsorber 40a. Adsorber 40 and bed 41 are then heated to suitable desorption temperature range such as 80°-100° C., by passing a heated inert gas 48 such as nitrogen heated at heater 49 through the bed to desorb it. The adsorbed water is withdrawn through conduit 52. Regenerated adsorber 40 is then ready for reintroducing ethanol-water stream 38 from the first-stage adsorption vessel 32 or 32a.

This invention is further described by the following example, which should not be construed as limiting the scope of the invention.

EXAMPLE 1

An ethanol-water solution containing 15 W % ethanol was passed through a vessel containing 400 cc of activated carbon adsorbent at conditions of about 20° C. temperature and atmospheric pressure. The activated carbon used was Nuchar HW-40, supplied by Westvaco Corp. A stream containing a reduced percentage of ethanol was withdrawn from the adsorbent bed. After about 30 minutes of such adsorption operation, the adsorption of ethanol on the carbon declined so that the effluent stream contained nearly the same percent ethanol as the feed stream, indicating substantial saturation of the adsorbent with ethanol.

Following such adsorption of ethanol on the carbon material, flow was stopped and the activated carbon was heated to about 80° C. and vapor containing about 80 W % ethanol was desorbed therefrom. Typical results of this first-stage adsorption-desorption cycle are shown in Table 1, based on 500 gm of feed liquid solution and using time-averaged results.

TABLE 1

| FIRST-STAGE ADSORPTION SEPARATION RESULTS | | | | | |
|---|---|---|---|---|---|
| | Alcohol, | | Water, | | Total |
| | gms | W % | gms | W % | W, gm |
| Feed Liquid | 75 | 15 | 425 | 85 | 500 |
| Effluent Liquid | 7 | 2 | 350 | 98 | 357 |
| Material Retained on Carbon Adsorbent | 72 | 50 | 71 | 50 | 143 |
| Vapor Composition Evolved Upon Desorption | 68 | 80 | 17 | 20 | 85 |

TABLE 1-continued

| FIRST-STAGE ADSORPTION SEPARATION RESULTS | | | | | |
|---|---|---|---|---|---|
| | Alcohol, | | Water, | | Total |
| | gms | W % | gms | W % | W, gm |
| Material Retained on Carbon after Desorption | 3 | 4 | 54 | 94 | 57 |

EXAMPLE 2

Further dehydration of the resulting ethanol-water mixture from Example 1 is achieved by a second adsorbent bed comtaining molecular sieves, using a procedure similar to that of Example 1. A vapor mixture from the first-stage adsorption step containing 20 W % water and 80 W % ethanol is passed through a container containing 400 cc of molecular sieve pellets Linde ® type 3A obtained from Union Carbide Corp. The adsorbent bed is maintained at temperature above 80° C. and operated at atmospheric pressure. This vapor, while ascending from the bottom of the bed to the top, is gradually stripped of water. Effluent vapor from the top of the bed is essentially anhydrous ethanol, which is passed to a condenser and collected as liquid product. After a sufficient time of operation, the molecular sieve adsorbent becomes substantially saturated with water and the effluent vapor shows an increasing water content. Flow is then stopped and the molecular sieve adsorbent, which now contains 20 W % of water, is heated to about 150° C. by a heated purging gas for desorption of water from the adsorbent. Typical results of this second-stage adsorption-desorption cycle are shown in Table 2.

TABLE 2

| SECOND-STAGE ADSORPTION SEPARATION RESULTS | | | | | |
|---|---|---|---|---|---|
| | Alcohol, | | Water, | | Total |
| | gms | W % | gms | W % | W, gm |
| Feed Vapor | 68 | 80 | 17 | 20 | 85 |
| Effluent Vapor Product | 66 | 99 | 1 | 1 | 67 |
| Material Retained on Molecular Sieves | 2 | 10 | 16 | 90 | 18 |

Alcohol in Feed to First Stage = 0.15 × 500 = 75 gm
Alcohol Recovered from Second-Stage Adsorber = 0.99 × 67 = 66 gm Based on the results presented in Tables 1 and 2, it is apparent that 66/75 or about 88 W % of the alcohol content of the feedstream is recovered using this adsorption process.

Although this invention has been described in terms of the accompanying drawings and preferred embodiment, it will be appreciated by those skilled in the art that many modifications and adaptions of the basic process are possible within the spirit and scope of the invention, which is defined solely by the following claims.

We claim:
1. A multi-stage adsorption process for separating an alcohol having boiling point lower than water from a water solution containing said alcohol in concentration less than 50 W %, comprising:
   (a) passing the feedstream solution through a first-stage bed of adsorbent material having higher affinity for the alcohol than for water, and adsorbing alcohol on the absorbent;
   (b) terminating the adsorption in the adsorbent bed, then heating said bed to a temperature sufficient to preferentially desorb the more volatile alcohol in vapor form from the adsorbent, and withdrawing a vapor stream having an increased concentration of the alcohol compared to the feedstream;
(c) passing the resulting desorbed vapor containing at least about 55 W % alcohol through a second-stage bed of adsorbent material selected to substantially adsorb the remaining water vapor; and
(d) withdrawing from said second-stage adsorbent bed a vapor product stream containing at least about 90 W % alcohol.

2. The process of claim 1, wherein liquid stream containing at least 60 W % water and some alcohol is withdrawn from step (a) and recycled to the feedstream to increase recovery of the alcohol.

3. The process of claim 1, wherein the alcohol vapor product desorbed from the second-stage adsorbent bed is condensed to form a dehydrated alcohol product.

4. The process of claim 1, wherein the adsorbent in each stage is heated indirectly to desorb the minor component.

5. The process of claim 1, wherein the adsorbent bed in each stage is heated directly and the minor component is desorbed by passing a heated inert gas through the beds.

6. The process of claim 1, wherein each stage of adsorption uses two adsorbent beds in which the minor component of the feedstream to each stage is adsorbed alternately, and the adsorbed fluid is desorbed by indirectly heating the bed with a hot fluid flowing through passageways embedded within each adsorbent bed.

7. The process of claim 1, wherein stages of adsorption are used, the feedstream to the first-stage bed contains less than about 50 W % alcohol, and the product from the second-stage bed contains less than about 2 W % water.

8. The process of claim 7, wherein the feedstream to step (a) contains 5-30 W % ethanol, and the product stream withdrawn at step (d) contains at least about 98 W % ethanol.

9. The process of claim 1, wherein the first-stage adsorbent is particulate activated carbon, and the adsorption conditions used in step (a) are within the range of 10°-60° C. temperature and 0-100 psig pressure.

10. The process of claim 1, wherein the second stage adsorbent is molecular sieve, and the adsorption conditions used in step (b) are 20°-80° C. temperature and 10-100 psig pressure.

11. A two-stage adsorption process for separating alcohols from an alcohol-water solution, comprising:
(a) passing the feedstream solution containing 5-30 W % alcohol through a bed of particulate-activated, carbon-adsorbent material, and adsorbing at least about 50 W % alcohol on the carbon;
(b) withdrawing an unadsorbed liquid stream containing mainly water;
(c) terminating the adsorption in the activated carbon bed, then heating said bed to temperature range of 50°-100° C. and preferentially desorbing the alcohol in vapor form from the carbon;
(d) withdrawing a vapor stream from step (c) having an increased concentration of alcohol relative to the feedstream, and passing the resulting vapor containing at least about 55 W % alcohol through a second-stage bed of a zeolite-adsorbent material to substantially adsorb the remaining water vapor;
(e) withdrawing from the second-stage adsorbent bed a product vapor stream containing at least about 95 W % purity alcohol; and
(f) heating the adsorbent material in the second-stage bed to desorb the water vapor and regenerate the adsorbent for reuse.

* * * * *